United States Patent [19]

Chao et al.

[11] 4,218,481

[45] Aug. 19, 1980

[54] YEAST AUTOLYSIS PROCESS

[75] Inventors: Kwei C. Chao; Edward F. McCarthy; George A. McConaghy, all of Naperville, Ill.

[73] Assignee: Standard Oil Company (Indiana), Chicago, Ill.

[21] Appl. No.: 949,207

[22] Filed: Oct. 6, 1978

[51] Int. Cl.² ............................................. A23J 1/18
[52] U.S. Cl. ....................................... 426/60; 426/62; 426/63; 435/267; 435/272
[58] Field of Search ................ 426/60, 62, 63; 195/4, 195/29, 82, 90, 97, 98; 435/267, 272

[56] References Cited

U.S. PATENT DOCUMENTS

| | | | |
|---|---|---|---|
| 2,217,264 | 10/1940 | Weizmann | 426/60 |
| 2,946,688 | 7/1960 | Rosenthal | 426/60 |
| 2,953,456 | 9/1960 | Mohler | 426/60 |
| 3,645,845 | 2/1972 | Corteel | 195/4 |
| 3,809,780 | 5/1974 | Ishida et al. | 426/60 |
| 3,975,553 | 8/1976 | Griffon | 426/60 |

*Primary Examiner*—Jeanette M. Hunter
*Attorney, Agent, or Firm*—Gregory E. Croft; William T. McClain; William H. Magidson

[57] ABSTRACT

Yeast autolysis is enhanced by the addition of certain exogenous enzymes to the yeast slurry at concentrations of from about 0.01–1.0 weight percent, said enzymes being selected from the group consisting of papain, ficin, bromelain, pancreatin, and aspergillus protease.

11 Claims, No Drawings

YEAST AUTOLYSIS PROCESS

BACKGROUND OF THE INVENTION

1. Field of the Invention

This invention relates generally to yeast autolysis processes and, more particularly, to a method for increasing the efficiency of yeast autolysis by the addition of certain exogeneous enzymes. The resulting yeast autolyzate is particularly effective as a growth stimulating nutrient for the preparation of dairy starter cultures for cheese making or other milk fermentations.

2. Description of the Prior Art

Autolyzed yeast and yeast autolyzate (also called autolyzed yeast extract), two different products from the yeast autolysis, have long been used as seasoning ingredients in the food industry. They are also important nutrient sources for various fermentation processes. Autolysis occurs when endogenous enzymes, mainly proteases and ribonucleases, digest the intracellular high molecular weight components of the yeast cells. The process can be induced by heating yeast to a temperature (about 50° C.) where the cell is killed, but the enzyme systems are active. It can be stimulated also by adding plasmolysing or liquefying agents such as salt and organic solvents. During autolysis, macromolecules are hydrolyzed and the soluble degradation products of small molecular size, such as peptides, amino acids, nucleotides, etc., diffuse out from the cells. It appears that the solubilization of organic nitrogenous material is the main aspect of autolysis.

Yeast autolysis can be carried out at temperatures ranging from about 30°–60° C. In general the process is extremely slow and at low temperatures may require 3–7 days for completion. At 50°–55° C., total digestion can be completed within 3 days, but in practice, shorter processing times are employed while sacrificing autolyzate yield. At the lower temperatures of 30°–40° C. the addition of antiseptics to suppress putrefaction is necessary, although antiseptics can be used at all temperatures to be safe. Generally used antiseptics are ethyl acetate, amyl acetate, toluene, formaldehyde, etc.

In a typical autolysis, a slurry or cream of live yeast cells (15–18 weight percent solids) is plasmolyzed with 2–5 weight percent salt (based on cell weight). Ethyl acetate is added as an antiseptic at 1% by volume to prevent bacterial growth. The slurry is heated up to 50°–55° C. and held at that temperature for 12–24 hours, or until the desired degree of solubilization is reached. The resulting autolyzed yeast material is then pasteurized at 80°–100° C., cooled, and centrifuged or filtered. The filtrate may be concentrated to a paste of about 70–80 weight percent solids, or spray dried to give a powdery yeast autolyzate product. Alternatively the autolyzed mixture may be directly spray dried without the removal of the cell debris to give an autolyzed yeast product. These two products are considerably different in their composition, flavor, and utility.

The use of exogenous enzymes to enhance the autolysis of yeasts is a new approach, although various enzymes have been used in a number of different processes. For example, U.S. Pat. No. 3,088,879 to Weaver teaches the use of papain as an initiator for liberating the cell contents of certain fungal cells containing a mycelial structure. In particular, the examples teach treatment of *Pencillium chrysogenum* and *Agaricus campestris* (mushroom). The treatment conditions taught are 50°–85° C. and a pH of 4.3–6.3. The reference does not suggest the applicability of papain to other microorganisms such as yeasts, and no mention is made of autolysis.

U.S. Pat. No. 3,523,801 to Shiga et al. teaches a nonautolytic process for preparing seasonings from microbial cells which includes initially subjecting the microbial cells to an alkaline solution for 1–3 hours at 50°–80° C. to destroy the cell walls, followed by neutralization and apparently a pasteurization step by heating at over 100° C. for 10–15 minutes The thus-treated cells are then treated with a suitable protease enzyme to decompose the proteins at 50°–60° C. for about 6–48 hours. This process involves a combined chemical and enzymatic treatment rather than an autolysis process.

U.S. Pat. No. 3,778,513 to Shiga et al. similarly teaches a method for preparing extract seasonings by first decomposing the cell walls with hydrochloric acid at 100°–130° C. for 1–5 hours. After neutralization, the decomposed material is subjected to a protease enzyme which breaks down the remaining protein to form a peptide mixture. Additional components are added to the peptide mixture and the mixture is subsequently heated and reached at 50°–80° C. for 0.5–5 hours to give a seasoning product. As is clear from the initial step, autolysis is not suggested by this reference since the cells would be inactivated by the high temperature acid treatment.

U.S. Pat. No. 3,809,780 to Ishida et al. teaches a method of preparing a seasoning agent wherein yeasts are subjected to specific cell lytic enzymes of the general *Coprinus, Daedaleopsis,* or *Irpex.* The yeast cells can be alive, although heat-killed cells are preferred. The cells are subjected to a decomposition by the enzyme at 45°–55° C. for 5–48 hours at a pH which is dependent upon the specific enzyme used. Although the decomposition conditions used in this process would promote autolysis if living cells were used, the reference clearly suggests that heat-killed cells are preferred, as indicated by the fact that all examples teach heat-treating of the cells at about 100° C. or more for about 10 minutes. Autolysis cannot occur after such a treatment because the enzymes would be inactivated. In addition, Ishida et al. teaches only the use of specific enzymes and does not suggest that any other enzymes will perform satisfactorily in such a process. It particularly does not suggest the enzymes of this invention in combination with autolysis.

As indicated, autolysis is a generally time-consuming process with low efficiency and poor quality assurance. In addition, it has been found that typical autolyzates, such as those produced by the use of plasmolyzing agents like sodium chloride, are poor growth stimulants for lactic acid bacteria starter cultures for making cheese. It is therefore an object of this invention to improve the yeast autolysis process, particularly increasing the yield of the yeast autolyzate and shortening the time needed for the completion of digestion. It is a further object of this invention to produce an effective growth stimulant for lactic acid bacteria starter cultures for making cheese.

SUMMARY OF THE INVENTION

Basically, the object of this invention is achieved by the continuous or batchwise addition of certain exogenous enzyme(s) to the autolytic system. The efficiency of yeast autolysis has been found to be greatly improved by adding at least one protease enzyme and/or a mixture enzyme containing protease, nuclease, lipase, and amylase as the digestive aid. In particular, the sulfhydryl proteases including papain, ficin, and bromelain, and the mixture enzymes, such as pancreatin or aspergillus proteases, are comparatively more effective in their synergistic effect on the autolysis. Papain, an FDA acceptable food-use protease is most effective for the purpose. A complete autolytic digestion of *C. utilis* cells can be obtained within 24 hours at an efficiency of 80–90% solubilization. Other yeasts can be expected to reach this degree of solubilization in less time, since *Candida utilis* is relatively more difficult to autolyze than many other yeasts. Other suitable yeasts specifically include *Saccharomyces cerevirial*, *Saccharomyces carlsbergensis*, and *Kluyveromyces fragilis*, although all yeasts are within the scope of this invention. The autolyzed material can be processed into autolyzed yeast by drying the whole mass, or into a completely water-soluble product of yeast autolyzate by removing the cell debris and then concentrating and/or spray drying. The products are particularly useful for stimulating lactic fermentation in cheese making.

The added exogenous enzyme(s) work in a synergistic fashion with the yeast endogenous enzymes to achieve the autolytic degradation of cellular material. The reasons are not understood, but two possible mechanisms can be suggested. One mechanism would be the direct attack on the yeast cell wall and/or membrane by the added enzyme(s) to disrupt the structure of the barrier. The cytoplasmic content of the cell, including endogenous enzymes, would be leached out to permit better interaction between the substrates and the enzymes. We have observed that when the yeast was autolyzed in the presence of papain, the yeast cell wall structure gradually disappeared as the digestion went on. This did not occur in the absence of papain. A second possible mechanism could be the situation wherein the autolysis was initiated from the action by the exogenous enzyme(s). Enzymes of small size (molecular weight of approximately 13,000, such as ribonuclease and 23,900, such as papain) are known to be able to penetrate through the yeast cell wall and membrane and act hydrolytically on the intracellular components. The resulting degradation could cause the disorganization of the cytoplasmic structure, therefore causing integration of the endogenous enzymes and substrate components which in tern accelerates the autolysis.

Among various enzymes acceptable for food uses, papain and pancreatin, used either separately or in combination, are the most effective. Papain, which is a commonly used protease, is relatively more effective in aiding yeast autolysis than is pancreatin. Pancreatin is a mixture enzyme system, containing protease, amylase, lipase, and nuclease. It has been observed that the combined use of pancreatin with papain during yeast autolysis improves the flavor of the final product to some extent.

In more specific terms, the invention resides in a process for autolyzing yeast comprising the steps of: (a) adding to an aqueous slurry of active yeast cells at least one enzyme selected from the group consisting of papain, ficin, bromelain, pancreatin, and aspergillus protease such that the concentration of said added enzyme(s) in the slurry is within the range of about 0.01–1.0 weight percent; and (b) maintaining the slurry containing the added enzyme(s) at a temperature of about 40°–60° C. and a pH of about 5.0–7.5 for about 2–24 hours with continuous mixing to yeild an autolyzed yeast slurry. The initial aqueous slurry of active yeast cells can preferably contain from about 10–20 weight percent cells on a dry weight basis, but the concentration is not critical. The resulting processed slurry can either be pasteurized and spray dried to give an autolyzed yeast product, or it can be further concentrated and clarified by stepwise centrifugation and spray dried to give a yeast autolyzate product. In the first instance, pasteurization can be accomplished by subjecting the autolyzed yeast slurry to temperatures of 80°–105° C. for about 1–30 minutes. The spray drying temperatures are preferably in the range of 140°–250° C./75°–100° C. (inlet/outlet). If a yeast autolyzate is desired, it is preferred that the autolyzed yeast slurry be centrifuged to first remove the cell debris, leaving a supernatant which contains solubilized materials. The supernatant is then concentrated under a vacuum at 50°–65° C. to about 30 weight percent solids. This concentrate is again centrifuged to remove any precipitated solids, and further concentrated under vacuum at 50°–65° C. to a paste of about 70–80 weight percent solids. As an alternative to the second concentration step, the centrifuged concentrate can be directly spray dried to give a powdery yeast autolyzate product.

The process of this invention is particularly interesting and useful in preparing an autolyzed yeast product which can be used as a growth-stimulating nutrient for the preparation of dairy starter cultures in cheese making or other milk fermentations. The addition of peptides, peptones, and amino acids is beneficial to the growth of lactic bacteria in culture media based on milk and/or whey. Protease-digested milk (by pepsin, trypsin, or papain) is usually used for this purpose. Yeast extracts are also used for this purpose but are relatively more expensive and less assured in quality. The autolyzed yeast product prepared by the process of this invention appears to have great potential in replacing these yeast extracts at least for this particular application.

DESCRIPTION OF SPECIFIC EMBODIMENTS

The following examples will serve to illustrate various aspects of this invention without limitation.

EXAMPLE 1.

*Candida utilis* (ATCC 9256) was grown on ethanol in a continuous fermentor operated under oxygen limited growth conditions. The yeast cells were centrifuged to give a yeast cream or slurry of 15% solids (dry weight basis). Aliquots of 25 ml. of the live cell slurry were distributed to each of several 70-ml tubes. Various enzymes, in solution form, were added to each sample to give a final enzyme concentration of 0.5% by weight. Ethyl acetate (0.25 ml) was added to each tube as an antiseptic for preventing bacterial putrefaction. The contents were mixed and each tube was stoppered. The tubes containing the autolytic material were incubated at 55° C. for 24 hours. The pH was around 6.0. The percentage of solubilization was determined from the dry weight of the total solids in the supernatant and the cell debris. The efficiency of various enzymes in aiding the autolysis in terms of solubilization of cellular material is presented in TABLE 1.

TABLE 1

| Enzyme Added | Solubilization of Cell, % |
| --- | --- |
| Control (no additive) | 37.8 |
| Papain | 78.4 |
| Ficin | 68.7 |
| Bromelain | 75.8 |

TABLE 1-continued

| Enzyme Added | Solubilization of Cell, % |
|---|---|
| Rennins | 39.5 |
| Pepsin | 41.8 |
| Trypsin | 37.6 |
| Pancreatin | 57.7 |
| Aspergillus Protease | 59.6 |

The most effective enzymes in aiding the yeast autolysis belong to the group of sulfhydryl proteases which includes papain, ficin, and bromelain. Papain is the most effective among these three proteases. Pancreatin and aspergillus protease, which are considered as mixtured enzymes, also are significantly effective in aiding the autolysis. The ineffectiveness of rennin, pepsin, and trypsin is not surprising, because the optimal pH for rennin, pepsin, and trypsin is 2.0, 3.5, and 8.0 respectively. The optimal pH for yeast autolytic enzymes, however, is about 5.0–6.5. The experiment was carried out at a pH of about 6.0.

EXAMPLE 2

A yeast cell cream containing 15% solids (dry weight basis) was pretreated by pasteurizing at 80° C. for 15 minutes. Both live cells and pasteurized cells were used as starting materials for the digestion experiment, both with and without the addition of 0.5% papain based on the cell dry weight. The experiment was carried out as described in Example 1. The results of solubilization are presented in TABLE 2.

TABLE 2

| Cells | Papain Added, % | Solubilization of Cells, % |
|---|---|---|
| Live | 0.0 | 36.7 |
| Live | 0.5 | 70.9 |
| Pasteurized | 0.0 | 17.7 |
| Pasteurized | 0.5 | 41.9 |

The results illustrate the enhanced effect of papain on the autolysis of yeast cells and the necessity for using live cells.

EXAMPLE 3

The autolysis experiment was carried out as described in Example 1, except that the dosage of papain varied from 0.01 to 0.3%, based on the cell dry weight, and the time of autolysis was 10 and 23 hours. The resulting autolyzed slurry was pasteurized at 95° C. for 15 minutes and then freeze dried. The samples were each evaluated for the percentage of solubilization and their the activity for the Milk Curdling Test. The solubilization results are presented in TABLE 3.

TABLE 3

| Papain Dosage, | Solubilization of Cells, % | |
| (grams per 100 grams of cells) | 10 hrs. | 23 hrs. |
|---|---|---|
| 0 | 39.8 | 40.7 |
| 0.01 | 51.6 | 66.8 |
| 0.03 | 57.7 | 73.6 |
| 0.10 | 65.6 | 79.8 |
| 0.30 | 72.3 | 84.2 |

The Milk Curdling Test is performed as follows: 10% nonfat dried milk (NFDM) containing the test sample (0.1–0.3 weight %) was pasteurized at 80°–85° C. for 5 minutes. The contents of the tube were cooled to 37° C. and inoculated with 1 ml. of diluted fresh inoculum of mixed culture of *Streptococcus thermophilus* and *Lactobacillus bulgaricus* (culture R-1 from Chr. Hansen's Lab.) prepared in 10% pasteurized NFDM. The inoculated tubes were incubated at 37° C. for observing the curd formation at various time periods. The normal clotting time should be about 4–5 hours. The results are presented in TABLE 4.

TABLE 4
Milk Curdling Test

| Testing Sample | | Sample Dosage, (grams per 100 cc. milk) | Curd Formation after Incubation |
|---|---|---|---|
| Control (none) | | | no curd |
| Commercial yeast extract | | 0.1 | soft curd |
| | | 0.2 | firm curd |
| | 0.01% papain | 0.1 | no curd |
| | | 0.2 | soft curd |
| | | 0.3 | soft curd |
| | 0.03% papain | 0.1 | soft curd |
| | | 0.2 | firm curd |
| | | 0.3 | firm curd |
| Autolyzed Yeast (10 hours digestion) | 0.1% papain | 0.1 | soft curd |
| | | 0.2 | firm curd |
| | | 0.3 | firm curd |
| | 0.3% papain | 0.1 | soft curd |
| | | 0.2 | firm curd |

| Testing Sample | | Sample Dosage, weight % | Curd Formation after Incubation |
|---|---|---|---|
| | 0.01% papain | 0.1 | soft curd |
| | | 0.2 | firm curd |
| | | 0.3 | firm curd |
| | 0.03% papain | 0.1 | soft curd |
| | | 0.2 | firm curd |
| | | 0.3 | firm curd |
| Autolyzed Yeast (23 hours digestion) | 0.1% papain | 0.1 | soft curd |
| | | 0.2 | firm curd |
| | 0.3% papain | 0.1 | soft curd |
| | | 0.2 | firm curd |

The results illustrate the effect of papain dosage and autolysis time in relation to the efficiency of solubilizing the cells. The milk curdling test results indicate that the autolyzed yeast product after 10 hours digestion with 0.1% papain or after 23 hours digestion with 0.01% papain is as effective as the reference yeast extract in stimulating the growth of the lactic starter culture.

EXAMPLE 4

364 lbs. of concentrated *Candida utilis* cells (15.3% cell concentration, dry weight basis) were heated to 55° C. in a 50 gallon jacketed tank. To this was added 25.3 gms. of crude papain. The mixture was stirred under 5 psig. nitrogen pressure for 12 hours while maintaining the temperature at 55° C. At the end of 12 hours the tank material was heated to 98° C. by direct injection of 30 psig. steam. It was held at 98° C. for 30 minutes and then cooled to 40° C. This material was then spray dried using an inlet air temperature of 160° C. and an exit air temperature of 85° C. The product was a fine, light tan powder containing 5.8% moisture. The initial yeast cream fed to the tank had 1.1% water soluble material, whereas by comparison the spray dried product had 66.2% water soluble material.

The product was tested in the previously described milk curdling test. Using no additive, after 4 hours the milk did not curdle. Using 0.2% of a commercial yeast extract the milk had a soft curd after 4 hours. Using 0.2% of the spray dried autolyzed yeast described it had a firm curd after 4 hours. These results show that the autolyzed yeast product made in the manner described is effective as a growth factor in cheese manufacture and is more effective on a weight basis than a yeast extract.

These examples are shown only for purposes of illustration and it will be apparent to those skilled in the art that many variations can be made therefrom without departing from the scope of this invention defined by the following claims.

We claim:

1. A process for autolyzing yeast comprising:
   (a) adding to an aqueous slurry of active yeast cells at least one enzyme selected from the group consisting of papain, ficin, bromelain, pancreatin, and aspergillus protease such that the concentration of said added enzyme(s) in the slurry is within the range of about 0.01 to about 1.0 percent by weight; and
   (b) incubating the slurry containing the added enzyme(s) at a temperature of about 40° to about 60° C. and a pH of about 5.0 to about 7.5 for about 2 to about 24 hours with continuous mixing to yield an autolyzed yeast slurry.

2. The process of claim 1 wherein the added enzyme is papain.

3. The process of claim 1 wherein the enzyme is pancreatin.

4. The process of claim 1 wherein the yeast is selected from the group consisting of *Candida utilis, Saccharomyces cerevisial, Saccharomyces carlsbergensis,* and *Kluyveromyces fragilis.*

5. The process of claim 1 wherein the temperature of step (c) is from about 50° to about 55° C.

6. The process of claim 1 wherein the autolyzed yeast slurry is pasteurized and spray dried to yield an utolyzed yeast product.

7. The process of claim 1 wherein the autolyzed yeast slurry is further processed by:
   (a) centrifuging to remove cell debris;
   (b) concentrating the resulting supernatant to about 30 weight percent solids (dry weight basis);
   (c) centrifuging the concentrated supernatant to remove any precipitated solids; and
   (d) spray drying the material from step (c) to yield a yeast autolyzate.

8. A process for autolyzing *Candida utilis* yeast comprising:
   (a) forming an aqueous slurry of active *Candida utilis* yeast cells having a cell concentration of about 15–20 weight percent (dry weight basis);
   (b) adding papain to the slurry such that the concentration of papain is within the range of about 0.01 to about 1.0 percent by weight;
   (c) incubating the slurry containing the added papain at a temperature of about 50°–55° C. and a pH of about 5.0–7.5 for about 2–24 hours with continuous mixing to yield an autolyzed yeast slurry; and
   (d) pasteurizing and spray drying the autolyzed yeast slurry to yield an autolyzed yeast product.

9. The autolyzed yeast product produced by the process of claim 6.

10. The yeast autolyzate product produced by the process of claim 7.

11. The autolyzed yeast product produced by the process of claim 8.

* * * * *